(12) United States Patent
Senoo

(10) Patent No.: US 9,375,148 B2
(45) Date of Patent: Jun. 28, 2016

(54) MOTOR DRIVE APPARATUS AND OPTICAL IMAGING APPARATUS FOR DIAGNOSIS

(75) Inventor: Tadashi Senoo, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 986 days.

(21) Appl. No.: 13/428,239

(22) Filed: Mar. 23, 2012

(65) Prior Publication Data

US 2012/0245459 A1 Sep. 27, 2012

(30) Foreign Application Priority Data

Mar. 24, 2011 (JP) ................................. 2011-066502

(51) Int. Cl.
*A61B 5/00* (2006.01)

(52) U.S. Cl.
CPC ............. *A61B 5/0066* (2013.01); *A61B 5/0084* (2013.01); *A61B 2560/045* (2013.01); *A61B 2562/228* (2013.01)

(58) Field of Classification Search
CPC .................................. A61B 5/00; A61B 5/0066
USPC ................................................. 600/473, 476
See application file for complete search history.

(56) References Cited

U.S. PATENT DOCUMENTS

| 6,134,459 | A | * | 10/2000 | Roberts et al. ................ 600/333 |
| 2006/0093276 | A1 | | 5/2006 | Bouma et al. |
| 2009/0086213 | A1 | * | 4/2009 | Masuda ........................ 356/479 |
| 2009/0251704 | A1 | | 10/2009 | Masuda |

FOREIGN PATENT DOCUMENTS

| JP | 05113520 A | 5/1993 |
| JP | 2005-196080 A | 7/2005 |

OTHER PUBLICATIONS

Extended European Search Report issued on Jul. 19, 2012, by the European Patent Office in corresponding European Patent Application No. 12160370.8-1265. (6 pages).

* cited by examiner

*Primary Examiner* — Peter Luong
(74) *Attorney, Agent, or Firm* — Buchanan, Ingersoll & Rooney PC

(57) ABSTRACT

A motor drive apparatus includes: a transmission unit carrying-out transmission of an optical signal between a rotation unit for rotating a transmitting and receiving unit and a fixation unit for transmitting reflected light to a control apparatus through a signal line, wherein the transmission unit includes: a tubular shaped lens holding member where a collimator lens is held, and a holding member fixing member having first fixation surface by which the end surface of the lens holding member is fixed and second fixation surface fixed by a surface which is formed to be approximately perpendicular to the direction toward which the optical signal is emanated or the optical signal is light-received; the first fixation surface is formed in a spherical shape; and the second fixation surface is formed to be approximately perpendicular to the direction toward which the optical signal is emanated or the optical signal is light-received.

23 Claims, 6 Drawing Sheets

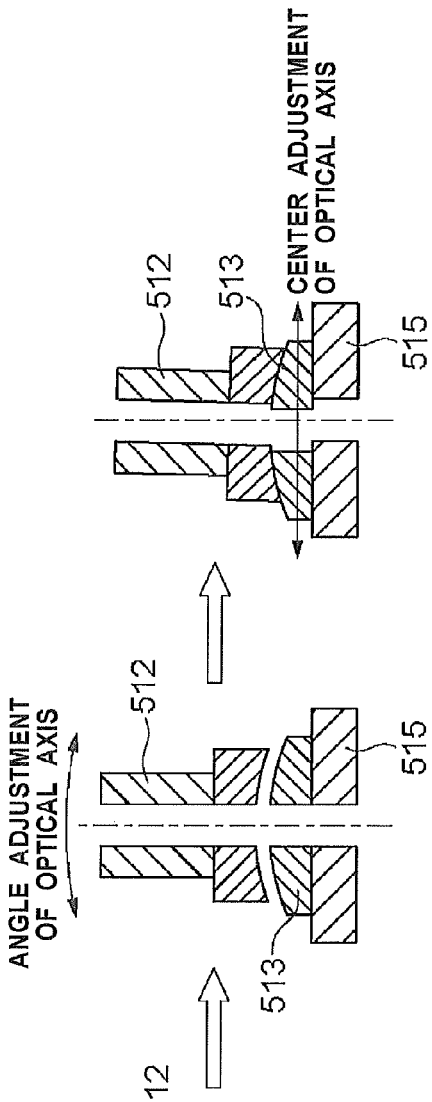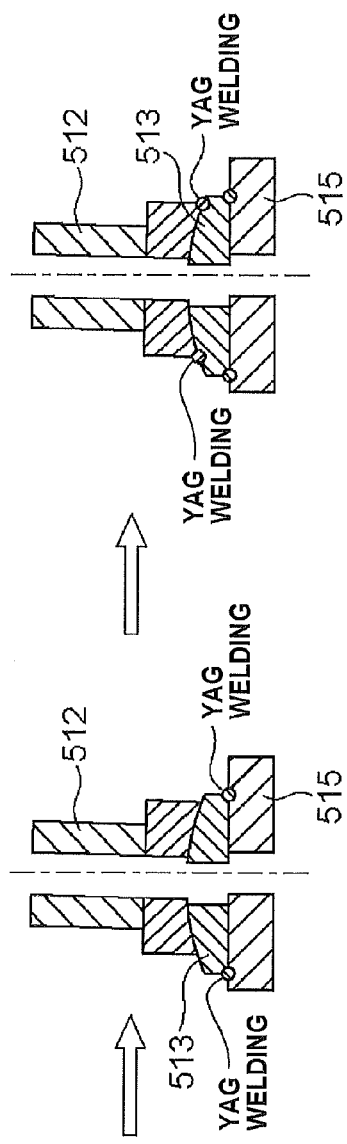

MOTOR DRIVE APPARATUS AND OPTICAL IMAGING APPARATUS FOR DIAGNOSIS

CROSS REFERENCES TO RELATED APPLICATIONS

The present invention contains subject matter related to Japanese Patent Application JP2011-066502 filed in the Japanese Patent Office on Mar. 24, 2011, the entire contents of which is incorporated herein by reference.

TECHNICAL FIELD

The present invention generally relates to a motor drive apparatus and an optical imaging apparatus for diagnosis.

BACKGROUND DISCUSSION

In the past, there have been used an optical coherent tomography (OCT) apparatus (see, for example, Japanese Unexamined Patent Publication No. 2005-196080) and an optical frequency domain imaging (OFDI) apparatus utilizing wavelength sweep, which is an improved type of apparatus for a diagnosis of arteriosclerosis, for a diagnosis before operation at the time of treatment inside a blood vessel depending on a high functional catheter such as a balloon catheter, a stent and the like or to confirm the result after an operation (hereinafter, in the present specification, the optical coherent tomography (OCT) apparatus and the optical frequency domain imaging (OFDI) apparatus utilizing wavelength sweep will be generically referred to as "optical imaging diagnostic apparatus").

In the optical imaging diagnostic apparatus, an optical probe unit inserted with an imaging core which is attached with an optical lens and an optical mirror (transmission and receiving unit) at a distal end of an optical fiber is inserted into a blood vessel, and a radial scan in a blood vessel is carried out by emitting a measurement light into the blood vessel from the transmitting and receiving unit at the distal end while rotating the imaging core and concurrently, by receiving a reflected light from a biological tissue. Then, an interference signal is generated by making the light-received reflected light and a reference light interfere with each other, and a cross-sectional image of the blood vessel is visualized based on the generated interference signal.

Here, for the radial scan of the imaging core, a motor drive apparatus referred to as a scanner & pull-back unit is generally utilized. The scanner & pull-back unit is constituted by a scanner unit and a pull-back unit, the scanner unit is mounted further with an optical probe unit detachably, and also, there are provided a rotation unit for rotating the imaging core inserted in the mounted optical probe unit and a fixation unit which repeats transmission of the measurement light and reception of the reflected light with respect to the rotating imaging core.

Then, the transmission and reception of the measurement light and the reflected light between the rotation unit and the fixation unit is usually carried out through collimator lenses respectively provided in the rotation unit and the fixation unit. Specifically, the measurement light emanated from the collimator lens provided in the fixation unit is light-received by the collimator lens provided in the rotation unit and the reflected light emanated from the collimator lens provided in the rotation unit is light-received by the collimator lens provided in the fixation unit.

Consequently, in order that an optical imaging apparatus for diagnosis visualizes a cross-sectional image of high image quality, it is important to suppress loss of the measurement light and the reflected light (these are referred to collectively as an optical signal) as much as possible between the two collimator lenses and for that purpose, it becomes indispensable to adjust the optical axes of both the collimator lenses highly accurately (such that the optical axis center tolerance and the optical axis angle tolerance fall within a predetermined range).

However, in the case of a conventional scanner & pull-back unit, a collimator lens was fixed, by using an adhesive agent, to a hollow tubular member for fixing the collimator lens. Consequently, the optical axis of the collimator lens which was adjusted before the hardening of the adhesive agent sometimes deviated due to the hardening and shrinkage of the adhesive agent. Further, in the conventional scanner & pull-back unit, once the collimator lens was fixed to the tubular member in this manner, it was difficult to fine-adjust the optical axis center and the optical axis angle anew. Due to such a fact, in an optical imaging apparatus for diagnosis, there is a demand for provision of a scanner & pull-back unit (motor drive apparatus) capable of highly accurately adjusting the optical axis between the collimator lenses in the rotation unit and in the fixation unit.

SUMMARY

The apparatus disclosed here is configured to reduce loss of an optical signal by employing a construction in which it is possible to adjust a collimator lens relatively highly accurately in a motor drive apparatus of an optical imaging apparatus for diagnosis.

The motor drive apparatus is mounted with an optical probe unit having a transmitting and receiving unit carrying out optical transmission and reception continuously, emitting measurement light while rotating the transmitting and receiving unit, obtaining reflected light from a biological tissue, which the transmitting and receiving unit receives, from the transmitting and receiving unit while moving in a body lumen in an axial direction and concurrently, transmitting the reflected light with respect to a control apparatus which can generate a plurality of cross-sectional images in the axial direction of the biological tissue by using the reflected light. The apparatus comprises a transmission unit carrying out transmission of an optical signal between a rotation unit for rotating the transmitting and receiving unit and a fixation unit for transmitting the reflected light to the control apparatus through a signal line. The transmission unit includes at least a tubular shaped lens holding member in the inside of which a collimator lens for emanating the optical signal or for light-receiving the optical signal is held, and a holding member fixing member having a first fixation surface by which the end surface of the lens holding member is fixed and a second fixation surface fixed by a surface which is formed so as to be approximately perpendicular to the direction toward which the optical signal is emanated or the optical signal is light-received the first fixation surface is formed in a spherical shape; and the second fixation surface is formed so as to be approximately perpendicular to the direction toward which the optical signal is emanated or the optical signal is light-received.

The motor drive apparatus of the optical imaging apparatus for diagnosis exhibits a reduction in the loss of an optical signal by employing a construction allowing adjustment of a collimator lens in a relatively highly accurate manner.

In accordance with another aspect, the transmission unit of the motor drive apparatus comprises: a tubular shaped lens holding member possessing an interior and opposite axial end surfaces; a collimator lens in the interior of the tubular shaped lens holding member, the collimator lens being connected to an optical fiber; a holding member fixing member having a first fixation surface at one axial end of the holding member fixing member and a second fixation surface at an opposite end of the holding member fixing member; the first fixation surface of the holding member fixing member being curved; with one of the axial end surfaces of the lens holding member being fixed to the curved first fixation surface; and the second fixation surface of the holding member fixing member being a flat surface approximately perpendicular to a direction along which the optical signal is emitted or the optical signal is light-received; wherein the flat second fixation surface is fixed to another surface.

According to another aspect, the transmission unit of the motor drive apparatus includes: a tubular-shaped lens holding member possessing an interior as well as opposite first and second axial end surfaces; a collimator lens in the interior of the tubular shaped lens holding member; and a holding member fixing member having a first fixation surface at one axial end of the holding member fixing member and a second fixation surface at an opposite end of the holding member fixing member. At least one of the first fixation surface of the holding member fixing member and the first axial end surface of the lens holding member is curved, with the first axial end surfaces of the lens holding member being fixed to the first fixation surface; and at least one of the second fixation surface of the holding member fixing member and a fixing surface being approximately perpendicular to a direction along which the optical signal is emitted or the optical signal is light-received, with the second fixation surface being fixed to the fixing surface.

BRIEF DESCRIPTION OF THE DRAWINGS

FIG. 6 is a diagram for explaining a procedure of adjusting an optical axis of a collimator lens.

DETAILED DESCRIPTION

Figure 1:
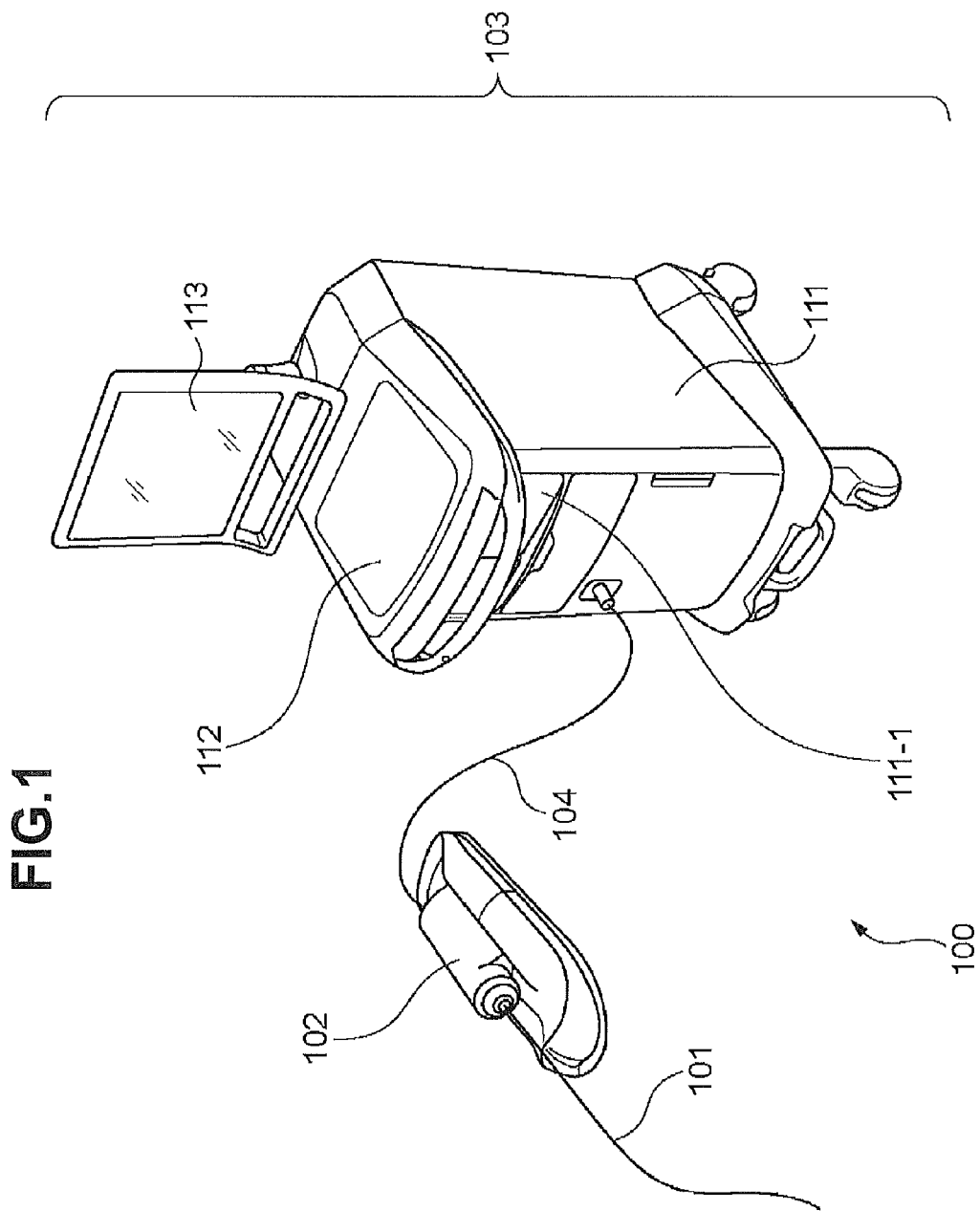
FIG. 1 is a diagram showing an outward-appearance constitution of an optical imaging apparatus for diagnosis relating to an exemplified embodiment.

The following detailed description will describe features and aspects of respective embodiments of an optical imaging apparatus disclosed here by way of example, while referring to the attached drawings.
First Embodiment
Outward-Appearance Construction of Optical Imaging Apparatus for Diagnosis FIG. 1 is a diagram showing an outward-appearance construction of an optical imaging apparatus for diagnosis (optical coherent tomography (OCT) apparatus or optical frequency domain imaging (OFDI) apparatus utilizing wavelength sweep) 100 relating to a first embodiment disclosed here by way of example. As shown in FIG. 1, the optical imaging diagnostic apparatus 100 is provided with an optical probe unit 101, a scanner & pull-back unit 102 and an operation control apparatus 103. The scanner & pull-back unit 102 and the operation control apparatus 103 are connected by a signal line 104.

The optical probe unit 101 is inserted directly into a body lumen of a biological tissue (blood vessel or the like) and transmits the transmitted measurement light continuously to the biological tissue and concurrently, there is inserted an imaging core provided with a transmission and receiving unit for receiving the reflected light from the biological tissue continuously and a state of the biological tissue is measured by using the imaging core. The scanner & pull-back unit (motor drive apparatus) 102 is constituted such that the optical probe unit 101 is mounted detachably therewith and there is realized a radial operation (operation in the axial direction and operation in the rotation direction inside the body lumen) of the imaging core inserted in the optical probe unit 101 depending on the driving of an installed motor. Also, the transmitting and receiving unit obtains the reflected light and concurrently, transmits the obtained reflected light to the operation control apparatus 103 through the signal line 104.

The operation control apparatus 103 is configured to permit various kinds of set values to be inputted when carrying out the measurement, to process data obtained by the measurement and to display them as a cross-sectional image of a biological tissue.

In the operation control apparatus 103, the reference numeral 111 indicates a main body control unit, and interference signal data are generated by making the reflected light obtained by the measurement and the reference light obtained by separating the measurement light interfere with each other, and concurrently, multiple cross-sectional images are generated in an axial direction of the body lumen by processing the line data generated based on the interference signal data. The reference numeral 111-1 indicates a printer & DVD recorder and it happens that the processed result in the main body control unit 111 is printed and is stored as data signals.

Figure 2:
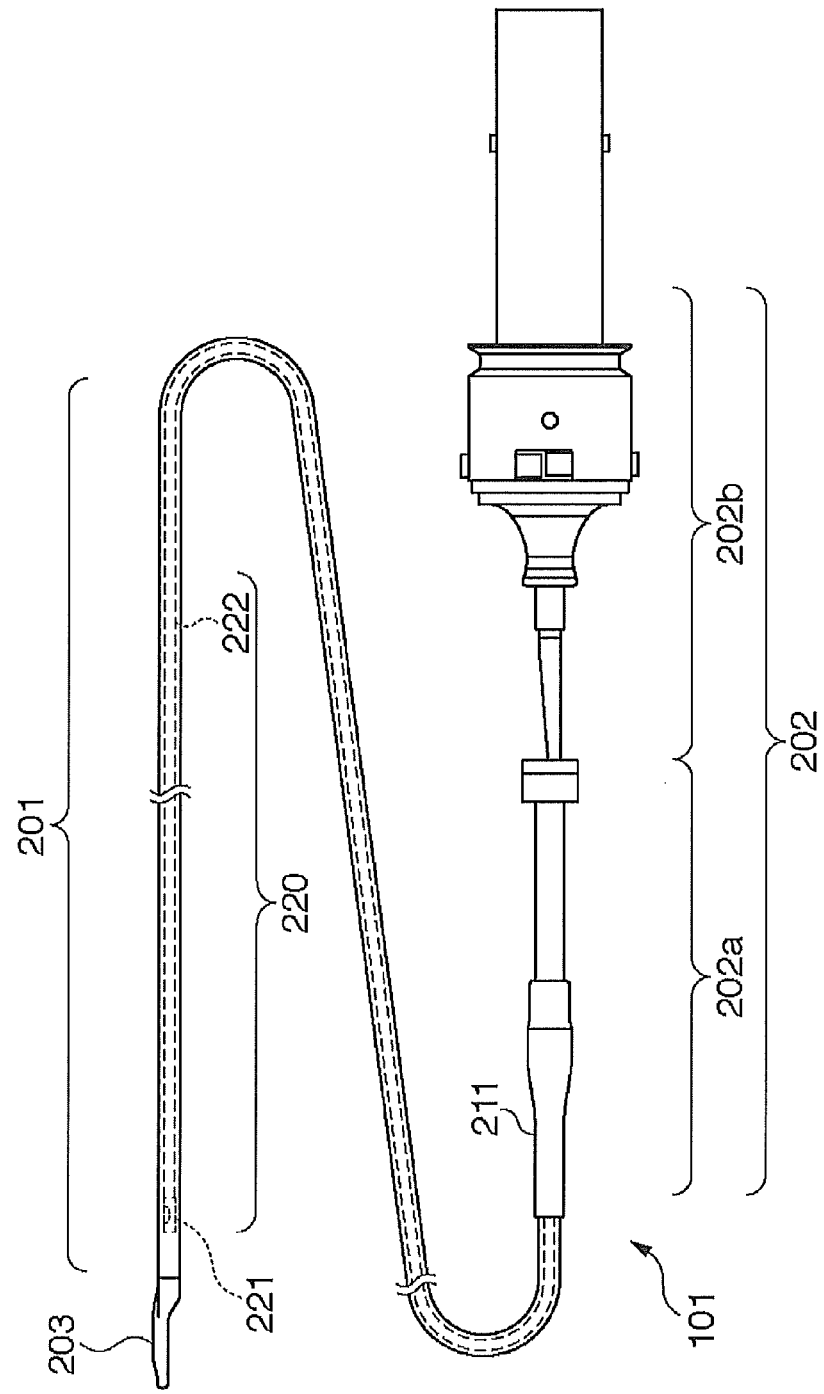
FIG. 2 is a diagram showing an outward-appearance constitution of an optical probe unit.

The reference numeral 112 indicates an operation panel and a user carries out input of various kinds of set values and instruction through the operation panel 112. The reference numeral 113 indicates an LCD monitor as a display apparatus and it displays a plurality of cross-sectional images of the biological tissue, which were generated in the main body control unit 111.
Overall Construction of Optical Probe Unit The description which follows describes, with reference to FIG. 2, the overall construction of the optical probe unit 101. As shown in FIG. 2, the optical probe unit 101 includes an elongated catheter sheath 201 to be inserted into a body lumen such as a blood vessel and the like, and a connector unit 202 which is not inserted inside the blood vessel in order to be steered by a user and which is arranged on the hand-side of a user (proximal side). The distal end of the catheter sheath 201 is provided with a tube 203 which constitutes a guide wire lumen, and the catheter sheath 201 is formed with a lumen which is continuous from a connection portion of the tube 203 toward a connection portion with the connector unit 202.

In the inside of a tubular lumen of a catheter sheath 201, there is inserted an imaging core 220, which includes a transmitting and receiving unit 221 for transmitting & receiving the measurement light and a drive shaft 222 including an optical fiber cable inside and transmitting drive force for rotating the cable, approximately over the full length of the catheter sheath 201 and the connector unit 202.

The connector unit 202 is provided with a sheath connector 202a constituted integrally at the proximal end of the catheter sheath 201 and a drive shaft connector 202b for supporting the drive shaft 222 rotatably at the proximal end of the drive shaft 222.

An anti-kink protector 211 is provided at a boundary portion between the sheath connector 202a and the catheter sheath 201 and thus, a predetermined rigidity is maintained and there is prevented a bend (kink) caused by a rapid physical property change.

Also, at the proximal end of the drive shaft connector 202b, there is arranged a mechanism for being attached to the scanner & pull-back unit 102 detachably.

Outward-Appearance Construction of Scanner & Pull-Back Unit

Figure 3:
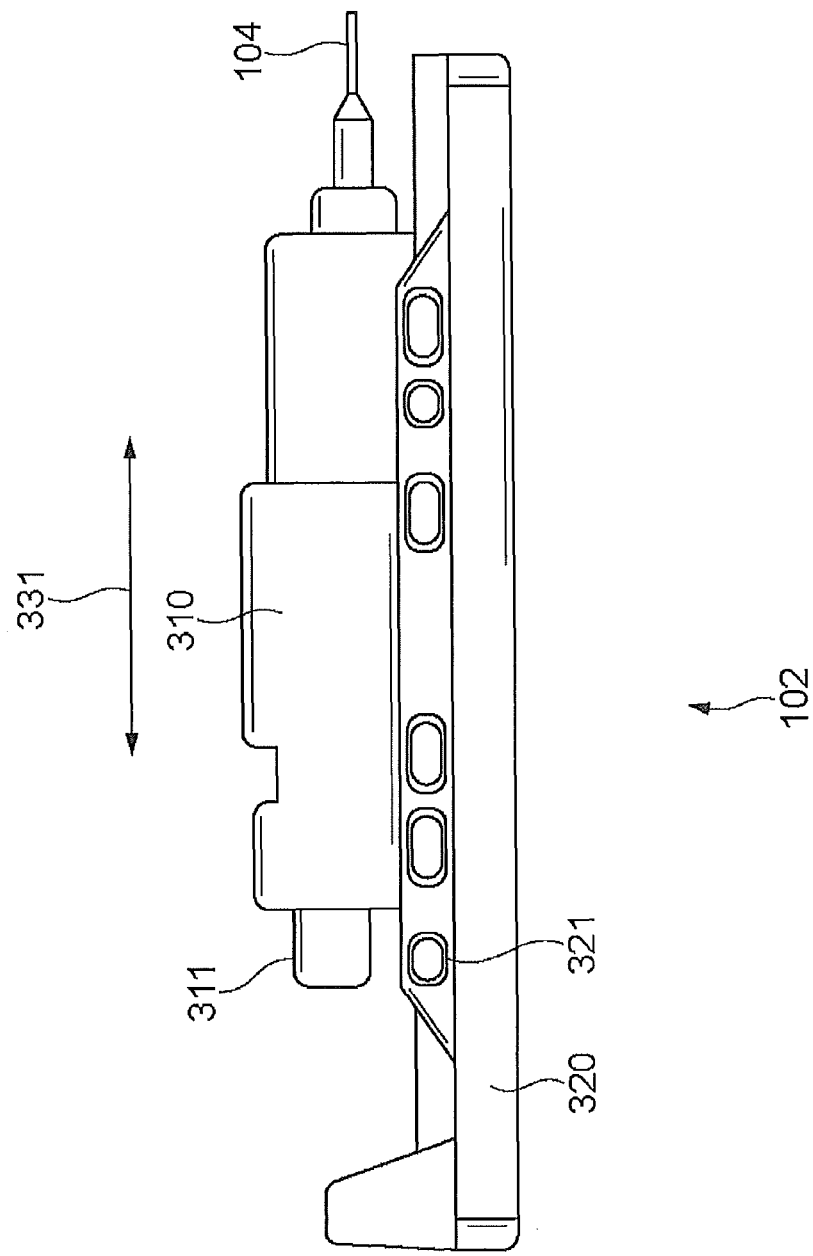
FIG. 3 is a diagram showing an outward-appearance constitution of a scanner & pull-back unit.

Set forth next with reference to FIG. 3 is a description of the outward-appearance configuration of the scanner & pull-back unit 102. As shown in FIG. 3, the scanner & pull-back unit 102 includes a scanner unit 310 where the drive shaft connector 202b of the optical probe unit 101 is mounted detachably at a mounting position 311 thereof and for rotating the imaging core 220 inserted into the optical probe unit 101, and a pull-back unit 320 which makes the imaging core 220 inserted into the optical probe unit 101 take a direct advance operation in an axial direction of the body lumen by making the scanner unit 310 mounted with the drive shaft connector 202b of the optical probe unit 101 take a direct advance operation in an axial direction (arrow 331 direction).

In the scanner unit 310, there is built-in a motor for rotational operation for rotating the imaging core 220 and there is realized a rotation speed of maximally 9600 rpm. Note that there is provided, between the rotation unit and the fixation unit of the scanner unit 310, with a transmission unit for carrying out transmission of an optical signal and it is constituted such that emanation & light-reception of an optical signal is carried out between the collimator lens on the rotation unit side and the collimator lens on the fixation unit side.

On the other hand, with respect to the pull-back unit 320, there is built therein a motor for direct advance operation for making the imaging core 220 take direct advance operation (move) in the axial direction of the body lumen. Note that there is disposed, on the side (near side of page face) of the pull-back unit 320, an instruction button 321 for instructing the rotation operation and the direct advance operation of the scanner & pull-back unit 102 and thus, it is possible for a user to instruct a desired operation with respect to the scanner & pull-back unit 102.

Cross-Sectional Construction of Scanner Unit

Figure 4:
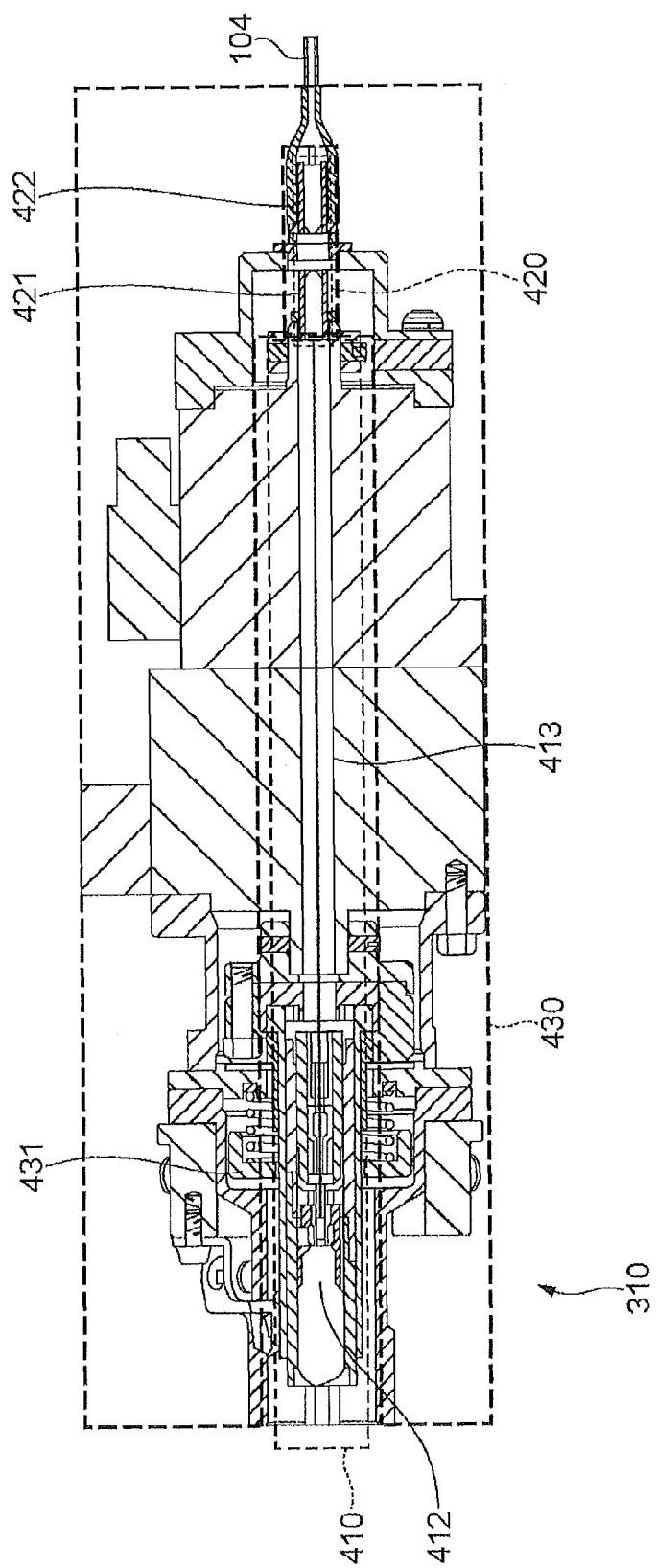
FIG. 4 is a diagram showing a cross-sectional constitution of a scanner unit.

Set forth next with reference to FIG. 4 is a description of the construction of the scanner unit 310 as seen in cross-section. As shown in FIG. 4, the scanner unit 310 generally includes a rotation unit 410 for rotating the imaging core 220 which is detachably mounted with the drive shaft connector 202b of the optical probe unit 101 and also which is inserted into the drive shaft connector 202b, a fixation unit 430 which supports the rotation unit 410 rotatably and concurrently, which is connected to the operation control apparatus 103 through the signal line 104, and a transmission unit 420 for carrying out transmission of an optical signal between the rotation unit 410 and the fixation unit 430.

The fixation unit 430 is, further, provided with a mounting mechanism 431 for attaching the drive shaft connector 202b of the optical probe unit 101 onto the mounting position 311 side. On the other hand, the fixation unit 430 is provided with an optical adaptor 412 which is coupled with an optical connector (not shown) arranged in the drive shaft connector 202b on the mounting position 311 side. Thus, attaching the drive shaft connector 202b of the optical probe unit 101 to the mounting mechanism 431 of the scanner unit 310 results in a state in which the optical connector and the optical adaptor 412 are coupled together, and optical connection between the imaging core 220 and the scanner unit 310 is realized.

The optical adaptor 412 in the rotation unit 410 is supported rotatably by the fixation unit 430 of the scanner unit 310 through a bearing which is not shown. Also, an optical fiber insertion portion 413, in which an optical fiber for transmitting an optical signal is inserted, is arranged between the optical adaptor 412 and the transmission unit 420, and it is constituted so as to be rotationally driven by a drive mechanism (including a motor for rotational operation, or the like) which is not shown. By way of such a construction, the rotational driving force received from the drive mechanism which is not shown is transmitted to the optical adaptor 412 through the optical fiber insertion portion 413, thereby making it possible to rotate the imaging core 220.

The transmission unit 420 is provided at the end portion on the side opposite to the optical adaptor 412 of the optical fiber insertion portion 413. The transmission unit 420 is constituted by a rotation side transmission unit 421 which is fixed at the end portion on the side opposite to the optical adaptor 412 of the optical fiber insertion portion 413 and a fixation side transmission unit 422 which is separated from the rotation side transmission unit 421 physically and which is fixed on the fixation unit 430 side. Note that the detailed constitution of the transmission unit 420 will be described later.

In the fixation unit 430, on the opposite side of the mounting position 311, there is connected the signal line 104 for transmitting and receiving a control signal for operating the optical signal transmitted by the fixation side transmission unit 422 and operating the drive mechanism which is not shown with respect to the operation control apparatus 103.

Cross-Sectional Construction of Transmission Unit

Figure 5:
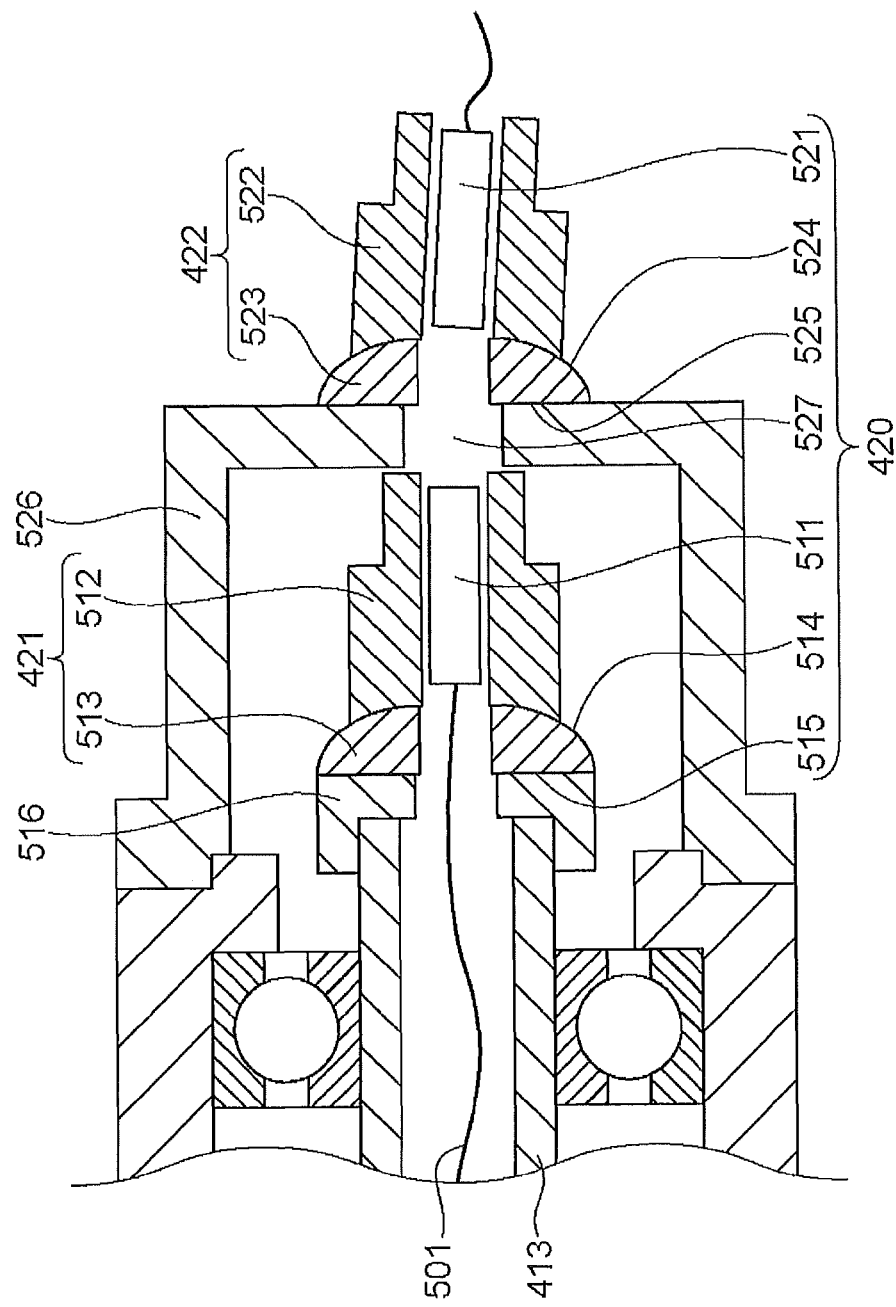
FIG. 5 is a schematic diagram showing a cross-sectional constitution of an optical transmission unit.

Set forth next with reference to FIG. 5 is a description of the construction of the transmission unit 420 as seen in cross-section. FIG. 5 schematically illustrates cross-sectional configurations of the end portion of the optical fiber insertion portion 413 and the transmission unit 420.

As shown in FIG. 5, the rotation side transmission unit 421 is provided with a collimator lens 511 for emanating an optical signal transmitted by an optical fiber 501, which is inserted into the optical fiber insertion portion 413, with respect to the fixation side transmission unit 422, and a tubular shaped lens holding member 512 for holding the collimator lens 511 in the hollow inside.

A holding member fixing member 513 is also provided for fixing the lens holding member 512. The holding member fixing member 513 is provided with a first fixation surface 514 which is a surface for fixing the lens holding member 512 and a second fixation surface 515 which is a surface contacting a base member 516 for fixing the holding member fixing member 513.

Here, the first fixation surface 514 possesses a curved or arcuate (non-planar of non-flat) shape. In the illustrated embodiment, the first fixation surface 514 possesses a spherical shape. Consequently, by sliding the axial end surface (curved or arcuate (non-planar of non-flat) axial end surface) of the lens holding member 512 along the first fixation surface 514, it is possible to fine-adjust the optical axis angle of the collimator lens 511 which the lens holding member 512 holds.

On the other hand, the second fixation surface 515 is a surface (flat surface) which is approximately perpendicular to the optical axis of the collimator lens 511 (approximately perpendicular to a direction toward which the optical signal is emitted or the optical signal is light-received). The second fixation surface 515 is fixed to a fixing surface (flat fixing surface), which in the illustrated embodiment is an axial end surface of the base member 516. This flat surface of the base member is approximately perpendicular to the optical axis of the collimator lens 511 (approximately perpendicular to a direction toward which the optical signal is emitted or the optical signal is light-received). By sliding the second fixation surface 515 on the end surface of the base member 516 likewise having a surface which is approximately perpendicular to the optical axis of the collimator lens 511, it is possible to fine-adjust the optical axis center of the collimator lens 511 which the lens holding member 512 holds.

With this construction, even in a case in which the collimator lens 511 is held by the lens holding member 512 with the optical axis center tolerance or the optical axis angle tolerance which exceeds the allowable range, it is possible to keep the optical axis angle tolerance within the allowable range by fine-adjusting the fixed position when fixing the lens holding member 512 on the holding member fixing member 513. Also, by fine-adjusting the fixed position when fixing the holding member fixing member 513 on which the lens holding member 512 is fixed to the base member 516, it is possible to keep the optical axis center tolerance within the allowable range.

On the other hand, the fixation side transmission unit 422 is provided with a collimator lens 521 for emanating the optical signal transmitted from the operation control apparatus 103 with respect to the rotation side transmission unit 421 and a tubular shaped lens holding member 522 which holds the collimator lens 521 in the hollow inside.

A holding member fixing member 523 is also provided for fixing the lens holding member 522. The holding member fixing member 523 is provided with a first fixation surface 524 which is a surface for fixing the lens holding member 522 and a second fixation surface 525 which is a surface contacting with the end surface of a fixation unit housing 526 to which the holding member fixing member 523 is fixed. The end surface of the fixation unit housing 526 is arranged between the lens holding member 512 and the lens holding member 522, and in the central position, there is provided an opening portion 527 for not blocking the optical signal which is transmitted between the collimator lens 511 and the collimator lens 521.

The first fixation surface 524 possesses a spherical shape. Consequently, by sliding the end surface of the lens holding member 522 along the first fixation surface 524, it is possible to fine-adjust the optical axis angle of the collimator lens 521 which the lens holding member 522 holds.

On the other hand, the second fixation surface 525 is a surface which is approximately perpendicular to the optical axis of the collimator lens 521, and by being slid on the end surface of the fixation unit housing 526 likewise having a surface which is approximately perpendicular to the optical axis of the collimator lens 521, it is possible to fine-adjust the optical axis center of the collimator lens 521 which the lens holding member 522 holds.

With this construction, even in a case in which the collimator lens 521 is held by the lens holding member 522 with the optical axis center tolerance or the optical axis angle tolerance which exceeds the allowable range, it is possible to keep the optical axis angle tolerance within the allowable range by fine-adjusting the fixed position when fixing the lens holding member 522 on the holding member fixing member 523. Also, by fine-adjusting the fixed position when fixing the holding member fixing member 523 on which the lens holding member 522 is fixed to the end surface of the fixation unit housing 526, it is possible to keep the optical axis center tolerance within the allowable range.

Procedure for Fine-Adjusting Optical Axis Collimator Lens

Set forth next with reference to FIG. 6 is an explanation of the procedure of fine-adjusting the optical axis of the collimator lens. FIG. 6 is a diagram showing a specific procedure of fine-adjusting the optical axis of the collimator lens, and is a diagram showing procedures in the rotation side transmission unit 421. The procedure in the fixation side transmission unit 422 is basically identical so that the description which follows regarding the procedure in the rotation side transmission unit 421 applies equally to the fixation side transmission unit.

As shown in FIG. 6, the holding member fixing member 513 is arranged with respect to the base member 516 fixed on the end surface of the optical fiber insertion portion 413 and further, the lens holding member 512 is arranged on the first fixation surface 514 of the holding member fixing member 513 (see FIG. 6A).

Next, by sliding the lens holding member 512 along the first fixation surface 514, the optical axis angle is adjusted (see FIG. 6B). Note that it is possible to confirm whether or not the optical axis angle deviates, by emanating an optical signal from the collimator lens 511 held by the lens holding member 512 and illuminating the illumination surface which is approximately perpendicular to the optical axis and arranged at the position which is a predetermined distance apart from the emanation position.

After the optical axis angle is fine-adjusted, the second fixation surface 515 of the holding member fixing member 513 is slid along the base member 516, and the optical axis center tolerance is fine-adjusted so as to fall within the allowable range (see FIG. 6C). After the holding member fixing member 513 is fine-adjusted to the predetermined position, the holding member fixing member 513 and the base member 516 are fixed by laser welding (YAG welding) (see FIG. 6D).

Further, the end surface of the lens holding member 512 is fixed by laser-welding (YAG welding) with respect to the first fixation surface 514 of the holding member fixing member 513 which is laser-welded with respect to the base member 516 (see FIG. 6E).

In this manner, the lens holding member 512 is constructed such that the peripheral portion of the end surface thereof contacts the first fixation surface on which the lens holding member 512 is fixed.

Consequently, it is possible to utilize the laser welding on an occasion when the lens holding member 512 is fixed on the first fixation surface.

Similarly, the holding member fixing member 513 is constructed such that at least the peripheral portion of the second fixation surface 515 contacts the second fixation surface 515 on which the holding member fixing member 513 is fixed. Consequently, it is possible to utilize the laser welding on an occasion when the holding member fixing member 513 is fixed on the base member 516.

As is clear from the explanation mentioned above, the scanner & pull-back unit 102 in this embodiment disclosed by way of example is constructed so that the holding member fixing members 513, 523 are arranged in order to fix the lens holding members 512, 522 which hold the collimator lenses 511, 521. Then, it is made to be a constitution in which the first fixation surfaces 514, 524 of the holding member fixing members 513, 523, on which the lens holding members 512, 522 are fixed, are formed in a spherical shape. Thus, by sliding the end surfaces of the lens holding members 512, 522 with respect to the first fixation surfaces 514, 524, it becomes possible to relatively easily fine-adjust the optical axis angles of the collimator lenses 511, 521 held by the lens holding members 512, 522. Also, by forming the end surfaces of the lens holding members 512, 522 in the shapes in which the peripheral portions thereof are contacted with the first fixation surfaces 514, 524, it is possible to fix the state after the fine-adjustment by the laser welding from the outside.

Further, the second fixation surfaces 515, 525 of the holding member fixing members 513, 523 are configured to be approximately perpendicular to the emanating direction or the light-receiving direction of the optical signal by the collimator lenses 511, 521. Thus, by sliding the second fixation surfaces 515, 525 with respect to the end surface of the base member 516 having the surface which is approximately perpendicular or the end surface of the fixation unit housing 526, it is possible to fine-adjust the optical axis centers of the collimator lenses 511, 521 held by the lens holding members 512, 522 which are fixed on the holding member fixing members 513, 523. Also, by forming the second fixation surfaces 515, 525 in the shapes in which the peripheral portions thereof are contacted with the end surface of the base member 516 or of the end surface of the fixation unit housing 526, it is possible to fix the state after the fine-adjustment by the laser welding from the outside.

As a result thereof, even in a case in which the collimator lenses 511, 521 are held in a state in which the optical axis center or the optical axis angle are deviated with respect to the lens holding members 512, 522, it is possible to fine-adjust it into the allowable range and also, to fix the state after fine adjustment by the welding from the outside. In other words, it is possible to adjust the collimator lens relatively highly accurately and it is also possible to reduce loss of the optical signal in the transmission unit 420.

Second Embodiment

In the first embodiment disclosed by way of example and described above, both the rotation side transmission unit 421 and the fixation side transmission unit 422 of the transmission unit 420 are constructed so that the optical axis center and the optical axis angle can be adjusted relatively highly accurately. But the invention here is not limited by this. With respect to either one, it is also possible to utilize a construction in which the optical axis center and the optical axis angle can be adjusted highly accurately.

Also, in the first embodiment disclosed by way of example and described above, the place of welding for the fixation by laser welding was not specifically described above. As an example, it is possible to weld three places at equal intervals in the circumferential direction at a peripheral portion of the end surface of each of the lens holding members 512, 522. Similarly, it is possible to weld three places at equal intervals in the circumferential direction at a peripheral portion of each of the second fixation surfaces 515, 525 of the holding member fixing member. Needless to say, the number of welding places is not to be limited to three as it is also possible to use four or more welding places.

The detailed description above describes features and aspects of embodiments of a motor drive apparatus and optical imaging apparatus for diagnosis disclosed by way of example. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A motor drive apparatus mounted with an optical probe unit having a transmitting and receiving unit carrying out optical transmission and reception continuously, emanating measurement light while rotating the transmitting and receiving unit, obtaining a reflected light from a biological tissue, which the transmitting and receiving unit receives, from the transmitting and receiving unit while moving in a body lumen in an axial direction and concurrently, transmitting the reflected light with respect to a control apparatus which generates a plurality of cross-sectional images in the axial direction of the biological tissue by using the reflected light, comprising:

a transmission unit carrying out transmission of an optical signal between a rotation unit for rotating the transmitting and receiving unit and a fixation unit for transmitting the reflected light to the control apparatus through a signal line;

the transmission unit comprising a rotation side transmission unit and a fixation side transmission unit with both the rotation side transmission unit and the fixation side transmission unit each having a tubular shaped lens holding member in an inside of which a collimator lens for emanating the optical signal or for receiving the optical signal is held;

wherein the rotation side transmission unit and the fixation side transmission unit each further include a holding member fixing member having a first fixation surface by which an end surface of the lens holding member is fixed and a second fixation surface configured to be fixed on a surface which is approximately perpendicular to the direction toward which the optical signal is emanated or the optical signal is received;

the first fixation surface having a spherical shape, the first fixation surface configured to be slidable with the end surface of the lens holding member for adjusting an optical axis angle of the collimator lens.

2. The motor drive apparatus according to claim 1, wherein:

the end surface of the lens holding member and the first fixation surface are fixed by laser welding; and the second fixation surface and the surface onto which the second fixation surface is fixed are fixed by laser welding.

3. The motor drive apparatus according to claim 2, wherein the surface onto which the second fixation surface is fixed is defined by an end surface of an optical fiber insertion portion into which an optical fiber connected to the collimator lens is inserted.

4. The motor drive apparatus according to claim 2, wherein the surface onto which the second fixation surface is fixed is defined by a surface of a fixation unit housing on which there is provided an opening portion for not blocking the optical signal.

5. An optical imaging apparatus for diagnosis comprising a motor drive apparatus according to claim 1, wherein a plurality of cross-sectional images in an axial direction of the biological tissue are generated based on line data of interference signal which is generated by interference of a reference light obtained by separating the measurement light and the reflected light transmitted from the motor drive apparatus.

6. A motor drive apparatus mounted with an optical probe unit having a transmitting and receiving unit carrying out optical transmission and reception continuously, emitting measurement light while rotating the transmitting and receiving unit, obtaining reflected light from biological tissue, which the transmitting and receiving unit receives, from the transmitting and receiving unit while moving in a body lumen in an axial direction and concurrently, transmitting the reflected light with respect to a control apparatus which generates a plurality of cross-sectional images in the axial direction of the biological tissue using the reflected light, comprising:
- a transmission unit which transmits an optical signal between a rotation unit that rotates the transmitting and receiving unit and a fixation unit that transmits the reflected light to the control apparatus through a signal line;
- the transmission unit comprising:
- a rotation side transmission unit and a fixation side transmission unit;
- the rotation side transmission unit and the fixation side transmission unit each including:
  - a tubular shaped lens holding member possessing an interior and opposite axial end surfaces;
  - a collimator lens in the interior of the tubular shaped lens holding member, the collimator lens being connected to an optical fiber;
  - a holding member fixing member having a first fixation surface at one axial end of the holding member fixing member and a second fixation surface at an opposite end of the holding member fixing member;
  - the first fixation surface of the holding member fixing member being spherical;
  - one of the axial end surfaces of the lens holding member being fixed to the spherical first fixation surface, the first fixation surface configured to be slidable with the one of the axial end surfaces of the lens holding member for adiusting an optical axis angle of the collimator lens;
  - the second fixation surface of the holding member fixing member being a flat surface approximately perpendicular to a direction along which the optical signal is emitted or the optical signal is light-received; and
  - the flat second fixation surface being fixed to a surface.

7. The motor drive apparatus according to claim 6, wherein the one axial end surface of the lens holding member which is fixed to the spherical first fixation surface is a spherical surface.

8. The motor drive apparatus according to claim 6, wherein the one axial end surface of the lens holding member which is fixed to the curved first fixation surface is a spherical surface.

9. The motor drive apparatus according to claim 8, wherein the first fixation surface of the holding member fixing member is a spherical surface.

10. The motor drive apparatus according to claim 6, wherein the first fixation surface of the holding member fixing member is a spherical surface.

11. The motor drive apparatus according to claim 6, wherein the one axial end surface of the lens holding member is welded to the curved first fixation surface.

12. The motor drive apparatus according to claim 6, wherein the flat second fixation surface of the holding member fixing member is welded to the surface.

13. The motor drive apparatus according to claim 6, wherein the surface, to which the flat second fixation surface of the holding member fixing member is fixed, is an end surface of an optical fiber insertion portion in which the optical fiber connected to the collimator lens is positioned.

14. The motor drive apparatus according to claim 6, wherein the surface to which the flat second fixation surface of the holding member fixing member is fixed is a surface of a fixation unit housing on which there is provided an opening portion for not blocking the optical signal.

15. A motor drive apparatus mounted with an optical probe unit having a transmitting and receiving unit carrying out optical transmission and reception continuously, emitting measurement light while rotating the transmitting and receiving unit, obtaining reflected light from biological tissue, which the transmitting and receiving unit receives, from the transmitting and receiving unit while moving in a body lumen in an axial direction and concurrently, transmitting the reflected light with respect to a control apparatus which generates a plurality of cross-sectional images in the axial direction of the biological tissue using the reflected light, comprising:
- a transmission unit which transmits an optical signal between a rotation unit that rotates the transmitting and receiving unit and a fixation unit that transmits the reflected light to the control apparatus through a signal line;
- the transmission unit comprising:
- a rotation side transmission unit and a fixation side transmission unit;
- the rotation side transmission unit and the fixation side transmission unit each including:
  - a tubular-shaped lens holding member possessing an interior, the tubular-shaped lens holding member also possessing opposite first and second axial end surfaces;
  - a collimator lens in the interior of the tubular shaped lens holding member;
  - a holding member fixing member having a first fixation surface at one axial end of the holding member fixing member and a second fixation surface at an opposite end of the holding member fixing member;
  - at least one of the first fixation surface of the holding member fixing member and the first axial end surface of the lens holding member being a spherical surface, the first fixation surface being configured to be slidable with the first axial end surface of the lens holding member for adiusting an optical axis angle of the collimator lens;
  - the first axial end surfaces of the lens holding member being fixed to the first fixation surface;
  - at least one of the second fixation surface of the holding member fixing member and a fixing surface being approximately perpendicular to a direction along which the optical signal is emitted or the optical signal is light-received; and
  - the second fixation surface being fixed to the fixing surface.

16. The motor drive apparatus according to claim 15, wherein the first axial end surfaces of the lens holding member is welded to the first fixation surface.

17. The motor drive apparatus according to claim 15, wherein the second fixation surface is welded to the fixing surface.

18. The motor drive apparatus according to claim 15, wherein the fixing surface, to which the second fixation surface of the holding member fixing member is fixed, is an end surface of an optical fiber insertion portion in which is positioned an optical fiber connected to the collimator lens.

19. The motor drive apparatus according to claim 15, wherein the fixing surface to which the second fixation surface of the holding member fixing member is fixed is a surface of a fixation unit housing on which there is provided an opening portion for not blocking the optical signal.

20. The motor drive apparatus according to claim 1, wherein the surface onto which the second fixation surface is approximately perpendicular to an optical axis of the collimator lens.

21. The motor drive apparatus according to claim 1, wherein the surface onto which the second fixation surface of the holding member fixing member of the fixation side transmission unit is fixed is arranged between the lens holding member of the rotation side transmission unit and the lens holding member of the fixation side transmission unit, and is defined by a surface of a fixation unit housing in which there is provided an opening portion for not blocking the optical signal.

22. The motor drive apparatus according to claim 6, wherein the surface, to which the flat second fixation surface is fixed, is approximately perpendicular to an optical axis of the collimator lens.

23. The motor drive apparatus according to claim 15, wherein the fixing surface is approximately perpendicular to an optical axis of the collimator lens.

\* \* \* \* \*